United States Patent
Shabtay et al.

(10) Patent No.: US 10,408,764 B2
(45) Date of Patent: Sep. 10, 2019

(54) SYSTEM, METHOD AND COMPUTER PROGRAM PRODUCT FOR OBJECT EXAMINATION

(71) Applicant: Applied Materials Israel Ltd., Rehovot OT (IL)

(72) Inventors: Saar Shabtay, Moshav Mishmeret (IL); Moshe Amzaleg, Beer Sheva (IL); Zvi Goren, Nes-Ziona (IL)

(73) Assignee: APPLIED MATERIALS ISRAEL LTD., Rehovot (IL)

( * ) Notice: Subject to any disclaimer, the term of this patent is extended or adjusted under 35 U.S.C. 154(b) by 0 days.

(21) Appl. No.: 15/703,937

(22) Filed: Sep. 13, 2017

(65) Prior Publication Data

US 2019/0079022 A1 Mar. 14, 2019

(51) Int. Cl.
| | |
|---|---|
| *G01N 21/88* | (2006.01) |
| *G06T 7/00* | (2017.01) |
| *G01N 21/95* | (2006.01) |
| *G01N 21/84* | (2006.01) |

(52) U.S. Cl.
CPC ..... *G01N 21/8803* (2013.01); *G01N 21/8851* (2013.01); *G01N 21/9501* (2013.01); *G06T 7/0004* (2013.01); *G06T 7/0006* (2013.01); *G01N 2021/8461* (2013.01); *G01N 2021/8867* (2013.01); *G06T 2207/10061* (2013.01); *G06T 2207/30148* (2013.01)

(58) Field of Classification Search
None
See application file for complete search history.

(56) References Cited

U.S. PATENT DOCUMENTS

| | | | | |
|---|---|---|---|---|
| 7,859,656 | B2* | 12/2010 | Uto | G01N 21/21 250/548 |
| 2009/0009753 | A1* | 1/2009 | Horai | G01N 21/65 356/237.3 |
| 2010/0128968 | A1* | 5/2010 | Cherbis | G06T 7/0004 382/141 |
| 2012/0206593 | A1* | 8/2012 | Shimodaira | G01N 21/8851 348/125 |
| 2013/0044208 | A1* | 2/2013 | Cherbis | G06K 9/209 348/125 |
| 2013/0294677 | A1* | 11/2013 | Urano | G01N 21/956 382/141 |

(Continued)

*Primary Examiner* — Jerome Grant, II
(74) *Attorney, Agent, or Firm* — Lowenstein Sandler LLP

(57) ABSTRACT

Examination system, method and computer-readable medium, the method comprising: processing by a processor using a first recipe at least one image comprised in images and metadata generated by an inspection tool and stored, to detect a first location set of first potential defects and attributes thereof; selecting and imaging part of the first location set with a review tool to obtain an image set; obtaining classification results of said first potential defects and determining a further recipe based thereon; processing the image using the further recipe for detecting a further location set of further defects; selecting part of the further location set; imaging the part with the review tool to obtain a further image set, and obtaining further classification results; and repeating determining the further recipe, processing the image, selecting and imaging part of the further location set, and obtaining further classification results, until a stopping criteria is met.

19 Claims, 4 Drawing Sheets

(56) References Cited

U.S. PATENT DOCUMENTS

| | | | |
|---|---|---|---|
| 2014/0031630 A1 | 1/2014 | Nguyen | |
| 2014/0241610 A1 | 8/2014 | Duffy et al. | |
| 2014/0253541 A1* | 9/2014 | Schmidt | G06T 19/20 345/419 |
| 2015/0083548 A1* | 3/2015 | Ackley | B07C 5/00 198/340 |
| 2015/0124247 A1 | 5/2015 | Park et al. | |
| 2015/0125065 A1 | 5/2015 | Lee et al. | |
| 2015/0178914 A1 | 6/2015 | Marella et al. | |
| 2015/0179400 A1 | 6/2015 | Lauber | |
| 2015/0234379 A1 | 8/2015 | Vajaria et al. | |
| 2015/0330912 A1 | 11/2015 | Gosain et al. | |
| 2015/0363537 A1 | 12/2015 | Kekare et al. | |
| 2016/0313285 A1* | 10/2016 | Lee | G01N 27/82 |
| 2016/0320265 A1* | 11/2016 | Regoli | G01M 17/027 |
| 2018/0246043 A1* | 8/2018 | Maibach | G01N 21/9081 |

\* cited by examiner

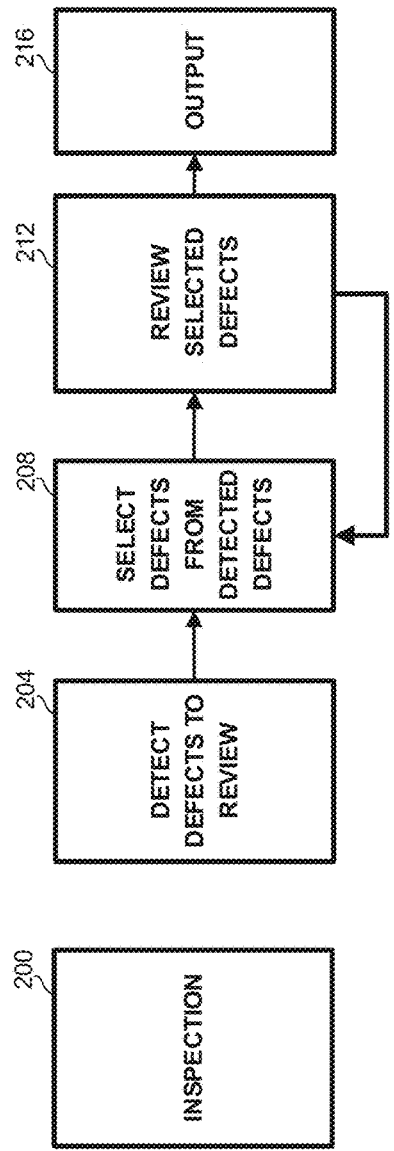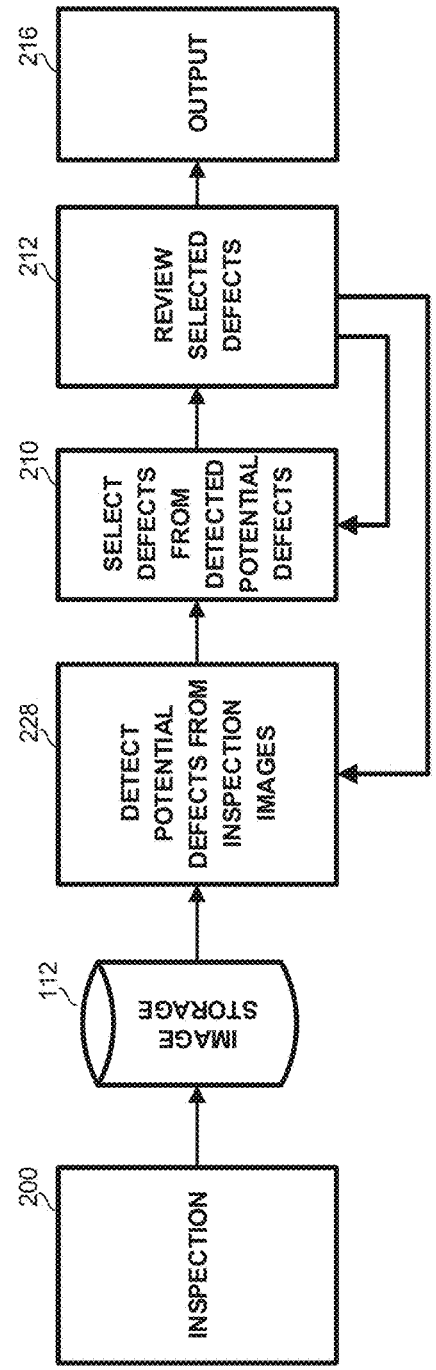

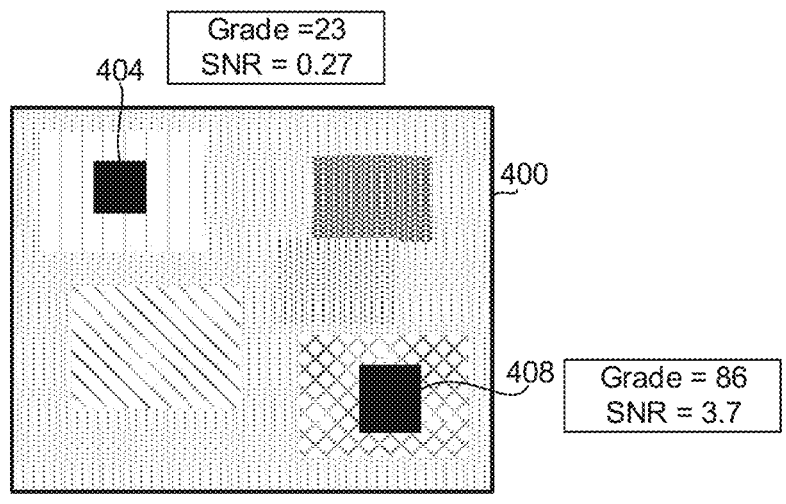
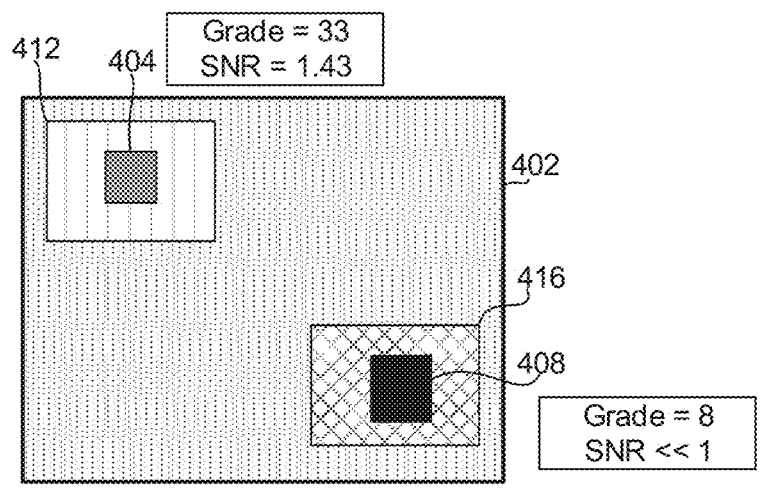
FIG. 4

SYSTEM, METHOD AND COMPUTER PROGRAM PRODUCT FOR OBJECT EXAMINATION

TECHNICAL FIELD

The presently disclosed subject matter relates to examining objects (e.g. wafers, reticles, etc.) and more particularly to detecting defects in objects by examining captured images of the objects.

BACKGROUND

Current demands for high density and performance, associated with ultra large scale integration of fabricated devices, require submicron features, increased transistor and circuit speeds, and improved reliability. Such demands require formation of device features with high precision and uniformity, which, in turn, necessitate careful monitoring of the fabrication process, including frequent and detailed inspection of the devices while they are still in the form of semiconductor wafers.

The terms "specimen" or "object" used in this specification should be expansively construed to cover any kind of wafer, masks, and other structures, combinations and/or parts thereof used for manufacturing semiconductor integrated circuits, magnetic heads, flat panel displays, and other semiconductor-fabricated articles.

The term "defect" used in this specification should be expansively construed to cover any kind of abnormality or undesirable feature formed on or within a wafer.

The complex manufacturing process of objects is not error-free and such errors may cause faults in the manufactured objects. The faults may include defects that can harm operation of the object, and nuisances, which may be defects, but do not cause any harm or malfunction of the manufactured unit. By way of non-limiting examples, defects may be caused during the manufacturing process, due to faults in the raw material; mechanical, electrical or optical errors; human errors or others. Further defects may be caused by spatio-temporal factors, such as temperature changes of the wafer occurring after one or more manufacturing stages during the examination process, which may cause some deformations of the wafer. The examination process can also introduce further alleged errors, for example due to optical, mechanical or electrical problems in the examination equipment or process, which thus provide imperfect captures. Such errors may produce false positive findings, which may seem to contain a defect, but no actual defect exists at the area.

In many applications, the type, or class, of a defect is of importance. For example, defects may be classified into one of a number of classes, such as a particle, a scratch, process, or the like.

Unless specifically stated otherwise, the term "image" used in the specification should be expansively construed to cover any non-destructive capturing of an object, including, but not limited to, capturing by an optical device, capturing by a scanning electron microscope, or by any other suitable device or tool.

Unless specifically stated otherwise, the term "examination" used in this specification should be expansively construed to cover any kind of detection and/or classification of defects in an object. Examination is provided by using non-destructive examination tools during or after manufacture of the object to be examined. By way of non-limiting example, the examination process can include scanning (in a single or in multiple scans), sampling, reviewing, measuring, classifying and/or other operations provided with regard to the object or parts thereof, using one or more examination tools. Likewise, examination can be provided prior to manufacture of the object to be examined and can include, for example, generating an examination recipe(s). It is noted that, unless specifically stated otherwise, the term "examination" or its derivatives used in this specification are not limited with respect to the size of the inspected area(s), to the speed or resolution of the scanning or to the type of examination tools. A variety of non-destructive examination tools includes, by way of non-limiting example, optical tools, scanning electron microscopes, atomic force microscopes, etc.

The examination process can include a plurality of examination steps. During the manufacturing process, the examination steps can be performed a multiplicity of times, for example after the manufacturing or processing of certain layers, or the like. Additionally or alternatively, each examination step can be repeated multiple times, for example for different wafer locations or for the same wafer locations with different examination settings.

By way of non-limiting example, run-time examination can employ a two-step procedure, e.g. inspection of a specimen followed by review of sampled defects. During the inspection step, the surface of a specimen or a part thereof (e.g. areas of interest, hot spots, etc.) is typically scanned at relatively high-speed and/or low-resolution. The captured inspection image is analyzed in order to detect defects and obtain locations and other inspection attributes thereof. At the review step the images of at least part of defects detected during the inspection phase are, typically, captured at relatively low speed and/or high-resolution, thereby enabling classification and, optionally, other analyses of the at least part of defects. In some cases both phases can be implemented by the same inspection tool, and, in some other cases, these two phases are implemented by different inspection tools.

SUMMARY

One aspect of the disclosed subject matter relates to an examination system comprising: a defect detection system comprising a processing and memory circuitry (PMC) and configured to receive inspection data comprising at least one inspection image informative of potential defects of an object; and a review tool configured to review at least part of the potential defects. PMC is configured to: upon accommodation in a memory the received inspection data, process the at least one image using a first recipe to detect a first set of locations of first potential defects and attributes thereof; select at least part of the first set of locations and image the selected at least part of the first set of locations with a review tool to obtain a first set of review images; based on the first set of review images, obtain first classification results informative of classification of at least part of the first potential defects corresponding to the selected at least part of the first set of locations; determine a further recipe using the first classification results; process the at least one image using the further recipe to detect a further set of locations of further potential defects and attributes thereof; select at least part of the further set of locations and image the selected at least part of the further set of locations with a review tool to obtain a further set of review images; based on the further set of review images, obtain further classification results informative of classification of at least part of the further potential defects corresponding to the selected at least part of the further set of locations; and repeat determining a next further recipe, processing the at least one image to detect a next further set of locations of a next further potential defects and attributes thereof, selecting at least part of the next further set of locations, imaging the at least part of the next further set of locations, and obtaining next further classification results, until an examination stopping criteria is met.

Within the examination system, detecting the further set of locations optionally comprises: segmenting the one or more of the images into segments in accordance with noise levels within each of the segments; determining a grade for elements within the segments, the grade indicative of a chance of each element to contain a defect; and detecting the further potential defects from elements of the segments in accordance with a threshold. Within the examination system, the inspection tool and the review tool are optionally one examination tool operated at different modes. Within the examination system, the PMB is optionally a part of the inspection tool. Within the examination system, the PMB is optionally a part of the review tool. Within the examination system, the PMB is optionally separate from the inspection tool and from the review tool.

Another aspect of the disclosed subject matter relates to a method of examining an object. The method comprises: processing, by the processor, using a first recipe at least one image to detect a first set of locations of first potential defects and attributes thereof, the at least one image comprised in inspection data generated by an inspection tool and stored in the memory; selecting, by the processor, at least part of the first set of locations and imaging by a review tool the selected at least part of the first set of locations with a review tool to obtain a first set of review images; based on the first set of review images, obtaining, by the processor, first classification results informative of classification of at least part of the first potential defects corresponding to the selected at least part of the first set of locations; determining, by the processor, a further recipe using the first classification results; processing, by the processor, the at least one image using the further recipe to detect a further set of locations of further potential defects and attributes thereof; selecting, by the processor, at least part of the further set of locations and imaging by the review tool the selected at least part of the further set of locations with a review tool to obtain a further set of review images; based on the further set of review images, obtaining, by the processor, further classification results informative of classification of at least part of the further potential defects corresponding to the selected at least part of the further set of locations; and repeating, by the processor, determining a next further recipe, processing the at least one image to detect a next further set of locations of a next further potential defects and attributes thereof, selecting at least part of the next further set of locations, imaging the at least part of the next further set of locations, and obtaining next further classification results, until an examination stopping criteria is met.

Within the method, one or more elements are optionally selected from the group consisting of: a pixel; a group of pixels; a feature and a geometrical area. Within the method, the further set of locations optionally does not include a location from a previous set of locations. The method can further comprise repeating said sampling the part of the further set of locations and obtaining further classification results per each further potential defect obtained, until a selection stopping criteria is met. Within the method, the selection stopping criteria is optionally selected from the group consisting of: all further set of locations have been reviewed, or a representative selection from the further set of locations has been reviewed. Within the method, the examination stopping criteria is optionally selected from the group consisting of: time allotted for examination is over; a number of review operations has reached a threshold; a number of true defects determined has reached a predetermined threshold; and a number of true defects determined on a previous one or more collections has decreased below a predetermined threshold. Within the method, classification is optionally into a true defect or a non-defect. Within the method, classification is optionally into a severe defect, a non-severe defect, a nuisance, or a false alarm. Within the method, obtaining the further recipe optionally uses classification results obtained with any previous recipe.

Yet another aspect of the disclosed subject matter relates to a non-transitory computer readable medium comprising instructions that, when executed by a computer, cause the computer to perform a method of examination of a semiconductor specimen as above.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 2A illustrates a generalized model of a prior art process of object examination;

FIG. 2B illustrates a generalized model of a process of object examination, in accordance with certain embodiments of the presently disclosed subject matter;

FIG. 4 shows an illustrative example of defect detection with segmentation, in accordance with certain embodiments of the presently disclosed subject matter.

DETAILED DESCRIPTION OF EMBODIMENTS

In the following detailed description, numerous specific details are set forth in order to provide a thorough understanding of the invention. However, it will be understood by those skilled in the art that the presently disclosed subject matter may be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "determining", "calculating", "processing", "computing", "representing", "comparing", "generating", "assessing", "matching", "processing", "selecting", "detecting", "sampling", "assigning" or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities including, by way of non-limiting example, an ADI system and parts thereof disclosed in the present application.

The terms "non-transitory memory" and "non-transitory storage medium" used herein should be expansively construed to cover any volatile or non-volatile computer memory suitable to the presently disclosed subject matter.

The term "recipe" refers to a set of parameters used by an imaging device such as an inspection device for capturing an object and analyzing the captured images. The recipe can include capture-related attributes such as light projecting conditions, light collection conditions, machine configuration, or others, and analysis-related parameters, such as noise level, thresholds for indicating a location as a potential defect, segmentation parameters, or others.

It is appreciated that, unless specifically stated otherwise, certain features of the presently disclosed subject matter, which are described in the context of separate embodiments, can also be provided in combination in a single embodiment. Conversely, various features of the presently disclosed subject matter, which are described in the context of a single embodiment, can also be provided separately or in any suitable sub-combination. In the following detailed description, numerous specific details are set forth in order to provide a thorough understanding of the methods and apparatus.

Figure 1:
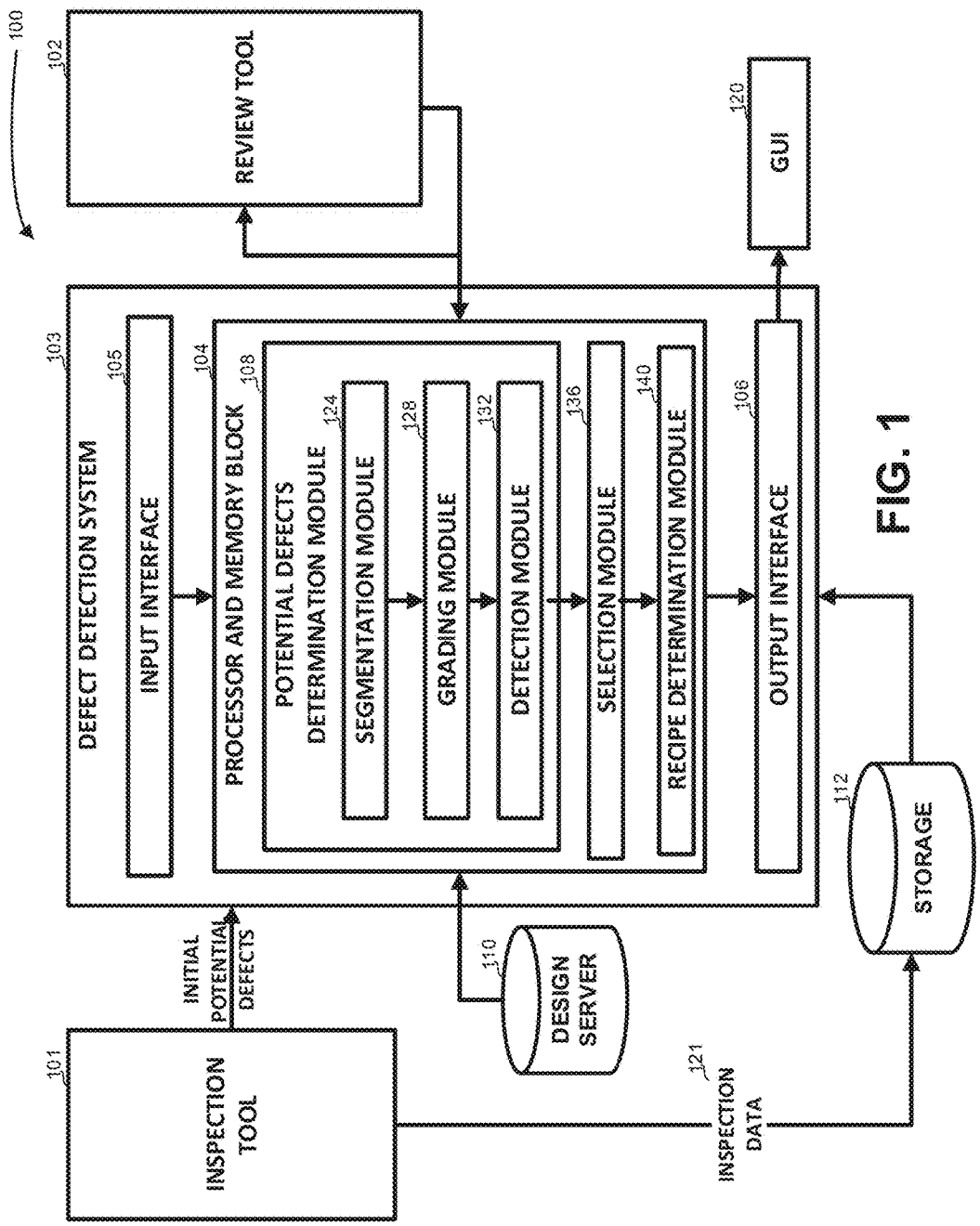
FIG. 1 illustrates a block diagram of an examination system, in accordance with certain embodiments of the presently disclosed subject matter.

Bearing this in mind, attention is drawn to FIG. 1 illustrating a block diagram of an examination system in accordance with certain embodiments of the presently disclosed subject matter. Examination system 100 illustrated in FIG. 1 can be used for examination of an object (e.g. a wafer and/or parts thereof) for defects as a part of object fabrication. The examination can be part of the object fabrication and can be carried out during manufacturing of the object, or afterwards. The illustrated examination system 100 comprises computer-based defect detection system 103 capable of automatically determining defect-related information using images obtained during or after object fabrication (referred to hereinafter as images), and/or derivatives thereof. Defect detection system 103 is referred to hereinafter as FPEI (Fabrication Process Examination Information) system 103. FPEI system 103 can be operatively connected to one or more inspection examination tools 101 and/or one or more review tools 102. Inspection tools 101 are configured to capture inspection images (typically, at relatively high-speed and/or low-resolution). Review tools 102 are configured to capture review images of at least part of defects detected by inspection tools 101 (typically, at relatively low-speed and/or high-resolution).

FPEI system 103 can be further operatively connected to design server 110 comprising design data of the object, such as Computer Aided Design (CAD) data.

An object can be examined by an inspection tool 101 (e.g. an optical inspection system, low-resolution SEM, etc.). The resulting images and/or derivatives thereof informative of revealed potential defects (collectively referred to hereinafter as inspection data 121) can be transmitted—directly or via one or more intermediate systems—to FPEI system 103. As will be further detailed with reference to the figures below, FPEI system 103 is configured to receive, via input interface 105, data produced by inspection tool 101 and/or data stored in design server 110 and/or another relevant data depository. Inspection data 121, including images and/or additional data or metadata can be stored in and retrieved from storage 112.

FPEI system 103 is further configured to process the received data and send, via output interface 106, the results (or part thereof) to a storage system, to examination tool(s), to a computer-based graphical user interface (GUI) 120 for rendering the results and/or to external systems (e.g. Yield Management System (YMS) of a FAB, recipe node, etc.). GUI 120 can be further configured to enable user-specified inputs related to operating FPEI system 103.

As will be further detailed with reference to the figures below, FPEI system 103 can be configured to process the received inspection data (optionally together with other data as, for example, design data and/or defect classification data) to select potential defects for review. It is noted that the potential defects for review are referred to hereinafter also as defects for review.

FPEI system 103 can send the processing results (e.g. instruction-related data) to any of the examination tool(s), store the results (e.g. defect classification) in a storage system, render the results via GUI 230 and/or send to an external system (e.g. to YMS, recipe node, etc.).

The specimen can be further examined by review tool 102. A subset of potential defect locations selected for review in accordance with data generated by FPEI system 103 can be reviewed by a scanning electron microscope (SEM) or Atomic Force Microscopy (AFM), etc. The resulting data informative of review images and/or derivatives thereof can be transmitted—directly or via one or more intermediate systems—to FPEI system 103 and can be used for further selection of potential defects for review, classifying the reviewed defects, etc.

FPEI system 103 comprises a processor and memory circuitry (PMC) 104 operatively connected to a hardware-based input interface 105 and to a hardware-based output interface 106. PMC 104 is configured to provide processing necessary for operating FPEI system 103 as further detailed with reference to the following figures and comprises a processor (not shown separately) and a memory (not shown separately). The processor of PMC 104 can be configured to execute several functional modules in accordance with computer-readable instructions implemented on a non-transitory computer-readable memory comprised in PMC 104. Such functional modules are referred to hereinafter as comprised in PMC 104. Functional modules comprised in PMC 104 can include defects determination module 108, selection module 136 and recipe determination module 140 Defects determination module 108 can include segmentation module 124, grading module 128 and detection module 132. Operating of PMC 104 and functional modules therein is further detailed with reference to FIG. 3.

It will be appreciated that inspection tool 101 and review tool 102 can be different tools located at the same or at different locations, or a single tool operated in two different modes. In the latter case, the tool may be first operated with lower resolution and high speed to obtain images of all or at least a large part of the relevant areas of the object. Once potential defects are detected, the tool can be operated at a higher resolution and possibly lower speed for examining specific locations associated with the potential defects.

Those versed in the art will readily appreciate that the teachings of the presently disclosed subject matter are not bound by the system illustrated in FIG. 1, and that equivalent and/or modified functionality can be consolidated or divided in another manner and can be implemented in any appropriate combination of software with firmware and hardware.

It is noted that FPEI system 103 illustrated in FIG. 1 can be implemented in a distributed computing environment, in which the aforementioned functional modules shown in FIG. 1 can be distributed over several local and/or remote devices, and can be linked through a communication network. It is further noted that in other embodiments at least some of examination tools 101 and/or 102, storage 112 and/or GUI 120 can be external to examination system 100 and operate in data communication with FPEI system 103, for example via input interface 105 and output interface 106. FPEI system 103 can be implemented as stand-alone computer(s) to be used in conjunction with the examination tools. Alternatively, the respective functions of FPEI system 103 can be, at least partly, integrated with one or more examination tools, process control tools, recipe generation tools, systems for automatic defects review and/or classification, and/or other systems related to examination. Unless explicitly indicated otherwise, the description below uses the terms "potential defects", "locations of potential defects" and "locations" interchangeably, since each defect may be identified by its location, each location may be a potential defect, and each defect may be verified by examining the respective location and possibly its surrounding area with a review tool.

Reference is now made to FIG. 2A, illustrating a generalized model of a prior art process of object examination.

The examination process starts by inspection tool 101 imaging (200) an object and capturing one or more images of an object to be examined. The images may cover the whole area of one or more layers in the object, or any part thereof. The images are taken and analyzed using a default recipe, or a recipe revised, for example, as a result of capturing a sample object of the type of the examined object. The recipe may indicate parameters such as one or more light conditions for capturing images.

An examination system analyzes the captured images and detects (204) a multiplicity of potential defects' locations. The analysis may also use additional parameters of the predetermined recipe for determining the potential defects, for example by using predetermined thresholds, preferring potential defects appearing in images taken under specific light conditions, or the like.

The examination system can then select (208) from the detected defects a multiplicity of locations for review. The locations can be selected as corresponding to potential defects having a highest probability to be true defects. Additionally or alternatively, the defects can be selected in a uniform distribution over the object area, or in accordance with other considerations.

The selected locations can then be imaged (212) by review tool 102, from which they can be classified. In some exemplary embodiments, the classification can be into a true defect or a false alarm. In other exemplary embodiments, further classes may be defined into which a potential defect can be classified, such as a defect, a severe defect, a nuisance, or a false alarm. Further classification can be into defect types, such as defects associated with a particular design feature, defects associated with layer mismatch, or the like.

The obtained results are output (216) to a user, a file, another system, or the like.

Based on the results of the imaging by review tool 102, further potential defects can be selected (208) from the potential defects as detected for review at 204.

The sampled potential defects are then imaged (212) using review 102.

Selecting 208 and imaging 212 can be repeated in a loop until one or more predetermined examination criteria are met, such as a maximal number of repetitions, a maximal number of true defects identified, a maximal number of review operations performed, a percentage of new true defects found in a predetermined number of repetitions being below a predetermined threshold, or others.

It is appreciated that in the flow of FIG. 2A, selection 208 is limited to the potential defects as detected on 204, such that the detection is not repeated, and potential defects that have not been detected from the inspection results will not be detected at a later time.

Reference is now made to FIG. 2B, illustrating a generalized model of a process of object examination, in accordance with certain embodiments of the presently disclosed subject matter.

The examination process starts by inspection tool 101 obtaining (200) one or more images of an object to be examined. The images may cover the whole area of one or more layers in the object, or any part thereof. The images are taken using a default recipe, or a recipe determined for example when capturing a sample object of the kind of the examined object.

The images, optionally with additional information such as attributes of the images or of specific locations therein, are stored in image storage 112, such as but not limited to a Network-attached storage (NAS) or solid-state drives (SSD), which is accessible to FPEI system 103.

It will be appreciated that while images of a first object are being stored within image storage 112, or processed by FPEI system 103, another object may already be imaged by inspection tool 101, thus increasing system throughput.

FPEI system 103 can then detect (228) defects from the inspection images as retrieved from image storage 112.

FPEI system 103 can then select (210) a multiplicity of defects' locations from the detected potential defects locations, to be examined by review tool 102.

The selected potential defects are then imaged (212) using review tool 102, and can then be classified.

The obtained classification results can be output (216) to a user, a file, another system, or the like.

The results can also be provided back to FPEI system 103, and a further multiplicity of potential defect locations can be selected (210) from the detected potential defects, imaged (212) by the inspection tool 102 and classified.

The selection 210 and imaging 212 can be repeated until a selection stopping criteria is met, meaning that the multiplicity of potential defects detected on 228 is exhausted, for example has been fully reviewed, the number of true defects identified by additional each repetition is below a predetermined threshold, or the like.

FPEI system 103 can then determine a new or updated recipe based on the classification results, and can use the new or updated recipe to detect (228) potential defects to be imaged by review tool 102. The detection is not limited to any potential defects previously detected for review. Rather, any location depicted in any of the images taken by inspection tool 101 and stored in image storage 112 can be detected, thus providing for a more efficient defect detection process, since the locations to be reviewed are chosen based on knowledge accumulated iteratively and are not limited to an initial list compiled under less information.

Thus, execution can return to detecting (228) potential defects from the inspection images as stored and not from a predetermined collection. The detected defects can but do not have to include additional potential defects not selected on previous selection steps.

FPEI system 103 can then select (210) and examine (212) locations from the currently selected potential defects with review tool 102. Selection 210 and examination 212 by review tool 102 can then repeat until the selection stopping criteria is met for the current detected defects.

The detection, followed by the selection, and review which may be repeated for each detection, can repeat until one or more examination stopping criteria is met, such as a maximal number of selection repetitions, a minimal or maximal number of true defects identified, a maximal number of review operations performed, a percentage of new true defects found in a predetermined number of repetitions being below a predetermined threshold, or the like.

Figure 3:
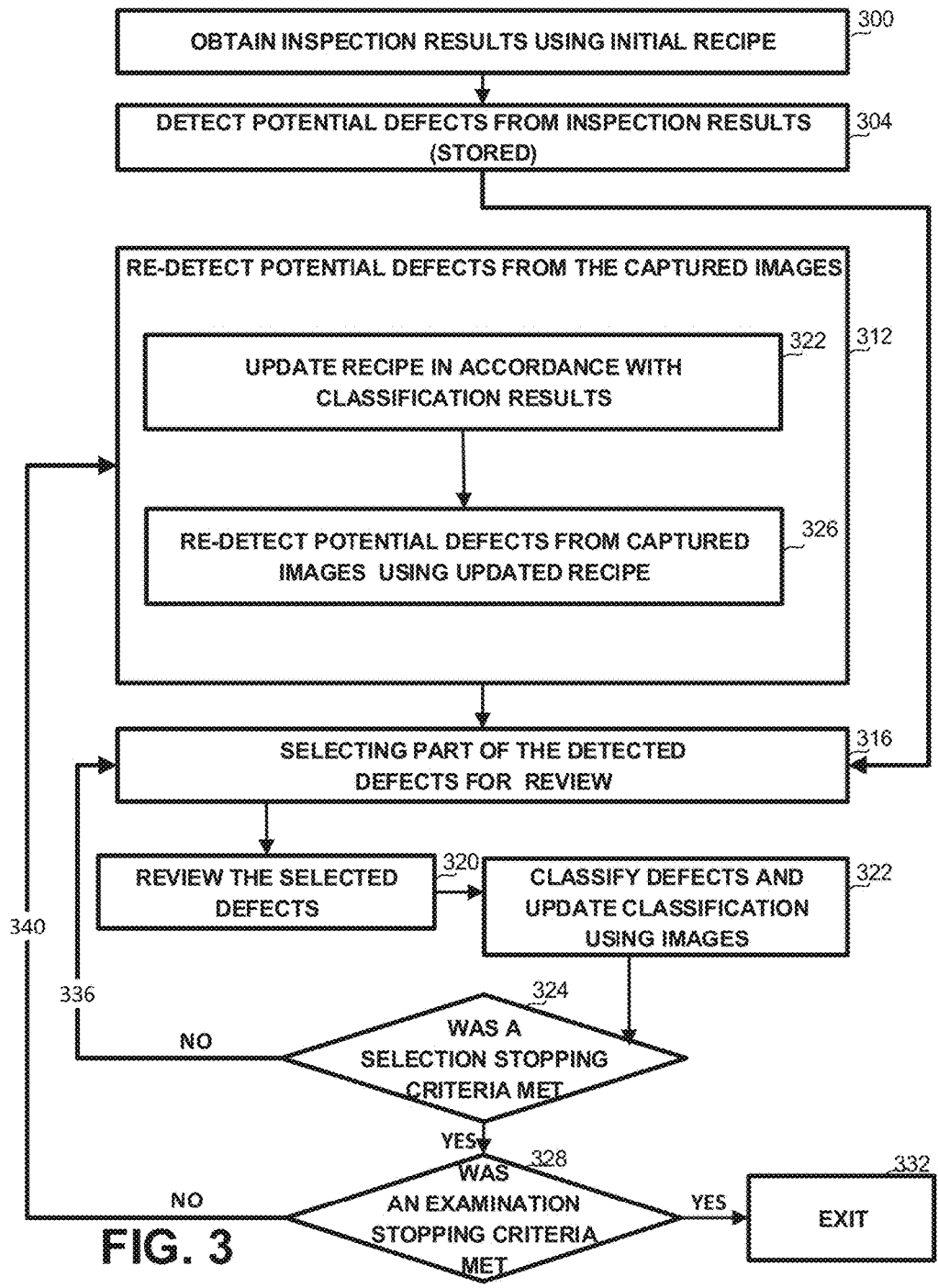
FIG. 3 illustrates a generalized flow-chart of an object examination process, in accordance with certain embodiments of the presently disclosed subject matter.

Reference is now made to FIG. 3, showing a generalized flowchart of a process of object examination, in accordance with certain embodiments of the presently disclosed subject matter.

FPEI system 103 can obtain (300), for example receive over a communication channel, read from a file, or the like, output of inspection of the object, including the images as captured and possibly additional data such as scanning parameters, meta data or the like. The captured images of the object may be stored, optionally together with the additional data, such as the scanning parameters, in image storage 112, to form an image data set.

FPEI system 103 can detect (304) potential defects from the output of inspection tool 101, using for example a recipe which may also have been used for capturing the images by inspection tool 101. The potential defects can be detected based on considerations such as providing uniform coverage to all areas, providing extra coverage to areas known to be problematic, using thresholds in accordance with the design data or the specific object, or the like.

Once potential defects are detected, FPEI system 103 can select (316) part of the potential defects for imaging by review tool 102. Selection 316 can be in accordance with considerations such as exploration vs. exploitation, region of interest (ROI), i.e. preferred areas, defect signature, or the like.

Review tool 102 can image (320) the locations of all or part of the potential defects.

Review tool 102 or FPEI system 103 can classify (322) the potential defects into the classes in accordance with the obtained images, to obtain further classification results and update the classification.

Once the classification results are available, FPEI system 103 can determine (324) whether a selection stopping criteria has been met, e.g., whether the selection has been exhausted in the sense that selecting additional potential defects for review from the further potential defects is not cost effective. Such a case can occur, for example, when all potential defects had been reviewed, when a representative part from the selection has been reviewed and no additional significant information is expected, enough candidates of a specific kind have been tested, budget or time limits have been met, or the like. It will be appreciated that one or more selection stopping criteria can be applied.

If no selection stopping criteria has been met, then execution returns (336) to selecting (316) yet another part of the potential defects, followed by imaging (320) and classifying (322).

If the selection stopping criteria has been met, FPEI system 103 can determine (328) whether an examination stopping criteria has been met, e.g., whether further potential defects should be determined for review beyond the ones already determined, or whether examination has been exhausted. The process may be determined to be exhausted if the time allotted for examination is over, if the number of review operations has reached a threshold, if the number of true defects determined has reached a predetermined threshold, if the number of true defects determined on the previous one or more collections has decreased below a predetermined threshold, or the like. It will be appreciated that one or more examination stopping criteria can be applied.

If the examination stopping criteria has been met, the process may exit (332). Additionally, results may be output, for example the true defects, statistics, or the like. It will be appreciated that certain results, such as true defects, may be output earlier, for example immediately after detection.

If the examination stopping criteria has not been met, execution can continue (340) to detecting a new collection of potential defects (312).

Using the classification results, FPEI system 103 and in particular potential defects determination module 108 can detect (312) potential defects from the inspection results, i.e., from the images as stored and the associated attributes. Rather, any location or area within the images captured by inspection tool 101 can be determined as a potential defect, whether it has been previously detected as a potential defect or not.

Detecting further potential defects (312) by FPEI system 103 can include updating the recipe (322), and using the updated recipe (326) for detecting the potential defects.

Recipe determination module 140 can determine (322) a new recipe or update the existing recipe in order to improve detection of the potential defects from the images taken by the inspection tool 101, which detection was initially done based on a default recipe determined upon one or more exemplary object setup wafers. Updating the recipe can comprise setting improved parameters for the segmentation. For example, polygon boundaries can be changed, segmentation can be re-applied with specific input, or the recipe can be changed such that areas with similar noise levels are segmented together. The default recipe with which the object is examined by the inspection tool, can produce segments each having a noise level or noise level range, such that multiple noise levels, for example in the order of magnitude of hundreds, may exist in segments within the images. Updating the recipe may relate to segmenting, i.e., grouping together areas having similar noise levels, in order to achieve a smaller number, for example a few, noise level ranges. The recipe may further relate to grading parameters and to thresholds associated with each such combined area, above which a defect is considered a true defect.

Typically, when determining potential defects, one or more images are segmented using the updated recipe, and potential defects are determined within each segment.

Reference is now also made to FIG. 4, showing an illustrative example of defect detection with segmentation, in accordance with certain embodiments of the presently disclosed subject matter. FIG. 4 shows image 400 in which areas 404 and 408 are detected by prior art solutions as potential defects. Areas 404 and 408 are graded, i.e. assigned a grade indicating their likelihood to be a true defect. Grading is done relative to the whole area of image 400, and thus area 404 is assigned a grade, i.e., a probability to be a defect of 23 with a signal to noise ratio of 0.27, and area 408 is assigned a grade of 86 with a signal to noise ratio of 3.7. Thus, area 408 is more likely to represent a defect than area 404. It will be appreciated that the background of FIG. 4 is generally less uniform than depicted, and comprises objects and a multiplicity of gray levels. The uniform background is therefore for explanatory purposes only.

In accordance with some exemplary embodiments of the disclosure, re-detecting the potential defects (326) may comprise segmenting one or more inspection images stored in image storage 112, or segmenting them in a different manner if the images have previously been segmented, such that the locations identified as potential defects are those locations which are more prominent within their respective segments. In some examples, the images may be segmented in accordance with the noise levels, such that the noise levels within each segment are relatively uniform or within a small range. A threshold may be associated with each segment, such that locations or areas within the segment exceeding the threshold are prominent and can be identified as potential defects. Pixel groups may be compared against other pixel groups within the same segment. If the groups are similar, the probability of these groups to represent a defect is decreased, as defects can be more random.

Image 402 of FIG. 4 shows areas 404 and 408 as above, wherein each is detected in a separate segment, such as segment 412 comprising area 404 and segment 416 comprising area 408. For example, a die (also referred to as a chip) may comprise areas arranged as one or more arrays, and other areas which are more chaotic. In some optical configurations of inspection tool 101, the arrays may reflect the light in a different manner than the other areas. By considering areas of relatively uniform nature, the number of gray levels within each area may be smaller than when array areas and non-array areas are comprised in one segment. For example, one area may comprise only 2-10 gray levels (out of the 256 possible gray levels). Thus, a gray level threshold differentiating between a potential defect and a normal location may be set such that defects which are depicted in gray levels other than these 2-10 gray levels are prominent and can be easily detected within such a segment. Other areas may be noisier and can comprise a larger number of gray levels, thus the threshold can be set to a different threshold than quiet areas. Setting the threshold in accordance with the noise level within each area provides for improved Signal to Noise Ratio (SNR) and thus better detection. Thus, in the example of FIG. 4, segments 412 and 416 are assigned different thresholds, which can make area 404 more prominent within segment 412 than area 408 within segment 416.

It will be appreciated that segmentation is more effective when performed using knowledge of some locations previously identified as potential defects and verified to be true defects or proven to be false alarms by the review tool. For example, using such classification information, it is known whether an area of a certain gray level within a larger area is part of the structure of the larger area, or is a defect, and the threshold for detecting defects within this larger area can be set accordingly. Thus, since by setting a specifically adapted threshold for each area, the potential defects can be more prominent and thus more easily detected. Unlike prior art solutions, in which the potential defects are determined based on inspection tool results, and further potential defects cannot be detected, the iterative manner disclosed above provides for making the process more efficient and detecting more true defects.

Even further, in prior art solutions, the same default setup and segmentation is used for all objects of a specific type. The disclosed solution, however, provides for adaptive setup of detection parameters ת including segmentation, in which the recipe used during defect detection is specifically adapted to the object and is also updated in accordance with newly acquired data to provide efficient defect detection.

It will be appreciated that segmentation is not necessarily associated with a geometric division of the object images, but other divisions can be used as well. For example, similar structures that are geometrically similar can be grouped together and be assigned the same or a similar threshold. In another example, it may be learned from the review imaging that many false alarms are located on specific areas or on specific features of the design of the object. Thus, these areas can be assigned an appropriate threshold, such that fewer defects will be detected therein. Additionally or alternatively, potential defects detected from specific areas may be selected for review (320) with lower priority. In another example, if the stored images comprise images from a multiplicity of scans, and more potential defects from one scan are proven to be true defects than from another scan, the second scan can be assigned a higher threshold or can even be ignored, such that more true defects will be detected.

Once the various areas are assigned thresholds, each location having a value that exceeds the threshold, for example becomes distinguishable from its environment, can be assigned a grade.

The segmentation and/or grading detailed below may utilize additional attributes which may be associated with each location, such as but not limited to any one or more of the following attributes: whether the location has a black or white background, whether the defect was detected on an image taken by a inspection tool with particular optic settings, the noise level in the environment of the location, or the like.

Re-detecting the potential defects may comprise grading, which can relate to assigning a probability to each location or each element which is prominent within its segment, e.g., exceeds the threshold, and can thus be a potential true defect. It will be appreciated that an element can refer to a location indicated as a pixel, as a group of connected pixels, as a feature, as a geometric shape, or the like. Grading may take into account how much the gray level of a specific location differs from the gray level of the locations of the respective segment; the gray level relative to neighboring locations within the segment, or the like. Grading can also take into account one or more of the attributes detailed above. Thus, the results of the grading are intensively affected by the segmentation and the threshold assigned to each segment, which in turn depend on the true/false information available for defects previously imaged by review tool 102. Additionally or alternatively, grading may comprise applying functions, for example convoluting the gray level values of the image with a function that gives a positive weight to the locations associated with potential true defects, and a negative weight to locations associated with false alarms, for example as follows: |f⊗Image|−|g⊗Image|, wherein f and g can be matched filters, such that the f filter matches a distinct shape associated with a true defect increases the grade of true defect, and the g filter matches a distinct shape associated with a false alarm.

Thus, such function or similar ones may provide for increased probability of true defects and decreased probability of false alarms. Thus, area 404 graded within segment 412 has a better SNR and is assigned a higher grade than area 408 graded within segment 416, which reverses their grading in respect to the whole image as shown on image 400.

In some embodiments, during grading a probability is assigned to the potential defects in a multiplicity of segments, such that all potential defects are on substantially the same scale and their grades can be compared, rather than the potential defects of each segment having their own scale.

It will be appreciated that initial grading may be performed for determining the initial potential defects, before any potential defect was imaged by review tool 102. However, the initial grading is based on the sample object and the default recipe, and does not rely on information regarding whether any potential defect is a true defect or a false alarm, and is thus significantly deficient.

Determination of the further potential defects can then be performed in accordance with the grading results and/or in accordance with thresholds. If, as described above, all potential defects are adjusted to be of substantially the same scale, the potential defects from all segments can be collected and sorted to form a unified list.

Selecting (316) part of the potential defects for imaging by review tool 102 can be performed in a multiplicity of ways. If the potential defects from all segments have been sorted into a unified list, the top predetermined number of potential defects can be selected, regardless of the segment they belong to. Alternatively, the same number of potential defects can be selected from each segment, wherein the highest graded potential defects are selected within each segment. In yet another embodiment, the number of potential defects selected from each segment is proportional to its area. It will be appreciated that further selection schemes may be designed without deviating from the disclosure.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the invention may be, at least partly, implemented on a suitably programmed computer. Likewise, the invention contemplates a computer program being readable by a computer for executing the method of the invention. The invention further contemplates a non-transitory computer-readable memory tangibly embodying a program of instructions executable by the computer for executing the method of the invention.

Those skilled in the art will readily appreciate that various modifications and changes can be applied to the embodiments of the invention as hereinbefore described without departing from its scope, defined in and by the appended claims.

The invention claimed is:

1. An examination system comprising:
   a defect detection system comprising a processing and memory circuitry (PMC) and to receive inspection data comprising at least one inspection image informative of potential defects of an object; and
   a review tool to review at least part of the potential defects, wherein the PMC is to:
   upon accommodation in a memory of the received inspection data, process the at least one inspection image using a first recipe to detect a first set of locations of first potential defects and attributes thereof;
   select at least part of the first set of locations and image the selected at least part of the first set of locations with the review tool to obtain a first set of review images;
   based on the first set of review images, obtain first classification results informative of classification of at least part of the first potential defects corresponding to the selected at least part of the first set of locations;
   determine a further recipe using the first classification results;
   process the at least one inspection image using the further recipe to detect a further set of locations of further potential defects and attributes thereof, wherein the further set of locations does not include a location from a previous set of locations associated with the at least one inspection image that includes potential defects that have been classified;
   select at least part of the further set of locations and image the selected at least part of the further set of locations with the review tool to obtain a further set of review images;
   based on the further set of review images, obtain further classification results informative of classification of at least part of the further potential defects corresponding to the selected at least part of the further set of locations; and
   repeat until an examination stopping criteria is met: determining a next further recipe, processing the at least one inspection image to detect a next further set of locations of a next further potential defects and attributes thereof, selecting at least part of the next further set of locations, imaging the at least part of the next further set of locations, and obtaining next further classification results.

2. The examination system of claim 1, wherein detecting the further set of locations comprises:
   segmenting the at least one image into segments in accordance with noise levels within each of the segments;
   determining a grade for elements within the segments, the grade being indicative of a chance of each element to contain a defect; and
   detecting the further potential defects from elements within the segments in accordance with a threshold.

3. The examination system of claim 1, wherein an inspection tool providing the inspection data and the review tool are one examination tool operated at different modes.

4. The examination system of claim 1, wherein the PMC is a part of an inspection tool providing the inspection data.

5. The examination system of claim 1, wherein the PMC is a part of the review tool.

6. The examination system of claim 1, wherein the PMC is separate from the review tool.

7. A method of examining an object using a processor operatively connected to a memory, the method comprising:
   processing, by the processor, at least one image by using a first recipe to detect a first set of locations of first potential defects and attributes thereof, the at least one image comprised in inspection data generated by an inspection tool and stored in the memory;
   selecting, by the processor, at least part of the first set of locations and imaging by a review tool the selected at least part of the first set of locations with the review tool to obtain a first set of review images;
   based on the first set of review images, obtaining, by the processor, first classification results informative of classification of at least part of the first potential defects corresponding to the selected at least part of the first set of locations;
   determining, by the processor, a further recipe using the first classification results;
   processing, by the processor, the at least one image using the further recipe to detect a further set of locations of further potential defects and attributes thereof, wherein the further set of locations does not include a location from a previous set of locations associated with the at least one image that includes potential defects that have been classified;
   selecting, by the processor, at least part of the further set of locations and imaging by the review tool the selected at least part of the further set of locations with a review tool to obtain a further set of review images;
   based on the further set of review images, obtaining, by the processor, further classification results informative of classification of at least part of the further potential defects corresponding to the selected at least part of the further set of locations; and repeating until an examination stopping criteria is met: determining, by the processor, a next further recipe, processing the at least one image to detect a next further set of locations of a next further potential defects and attributes thereof, selecting at least part of the next further set of locations, imaging the at least part of the next further set of locations, and obtaining next further classification results.

8. The method of claim 7, wherein detecting the further set of locations comprises:

segmenting the at least one image into segments in accordance with noise levels within each of the segments;

determining a grade for elements within the segments, the grade being indicative of a chance of each element to contain a defect; and detecting the further potential defects from elements within the segments in accordance with a threshold.

9. The method of claim 8, wherein at least one element is selected from one or more of: a pixel; a group of pixels; a feature and a geometrical area.

10. The method of claim 7, further comprising repeating until a selection stopping criteria is met: selecting at least part of the further set of locations and obtaining further classification results.

11. The method of claim 10 wherein the selection stopping criteria is selected from one or more of: all further set of locations have been reviewed, and a representative selection from the further set of locations has been reviewed.

12. The method of claim 7, wherein the examination stopping criteria is selected from one or more of: time allotted for examination is over, a number of review operations has reached a threshold, a number of true defects determined has reached a predetermined threshold, and a number of true defects determined on a previous one or more collections has decreased below a predetermined threshold.

13. The method of claim 7, wherein the classification is into a true defect or a non-defect.

14. The method of claim 7, wherein the classification is into a severe defect, a non-severe defect, a nuisance, or a false alarm.

15. The method of claim 7, wherein obtaining the further recipe uses classification results obtained with any previous recipe.

16. A non-transitory computer readable medium comprising instructions that, when executed by a processor, cause the processor to perform operations comprising:

processing, by the processor, at least one image by using a first recipe to detect a first set of locations of first potential defects and attributes thereof, the at least one image comprised in inspection data generated by an inspection tool and stored in the memory;

selecting, by the processor, at least part of the first set of locations and imaging by a review tool the selected at least part of the first set of locations with the review tool to obtain a first set of review images;

based on the first set of review images, obtaining, by the processor, first classification results informative of classification of at least part of the first potential defects corresponding to the selected at least part of the first set of locations;

determining, by the processor, a further recipe using the first classification results;

processing, by the processor, the at least one image using the further recipe to detect a further set of locations of further potential defects and attributes thereof, wherein the further set of locations does not include a location from a previous set of locations associated with the at least one image that includes potential defects that have been classified;

selecting, by the processor, at least part of the further set of locations and imaging by the review tool the selected at least part of the further set of locations with a review tool to obtain a further set of review images;

based on the further set of review images, obtaining, by the processor, further classification results informative of classification of at least part of the further potential defects corresponding to the selected at least part of the further set of locations; and repeating until an examination stopping criteria is met: determining, by the processor, a next further recipe, processing the at least one image to detect a next further set of locations of a next further potential defects and attributes thereof, selecting at least part of the next further set of locations, imaging the at least part of the next further set of locations, and obtaining next further classification results.

17. The non-transitory computer readable medium of claim 16, wherein to detect the further set of locations, the operations further comprise:

segmenting the at least one image into segments in accordance with noise levels within each of the segments;

determining a grade for elements within the segments, the grade being indicative of a chance of each element to contain a defect; and detecting the further potential defects from elements of the segments in accordance with a threshold.

18. The non-transitory computer readable medium of claim 16, wherein the operations further comprise:

repeating until a selection stopping criteria is met: selecting at least part of the further set of locations and obtaining further classification results.

19. The non-transitory computer readable medium of claim 16, wherein the classification is into a true defect or a non-defect.

* * * * *